United States Patent [19]
Spinello

[11] Patent Number: 5,693,026
[45] Date of Patent: Dec. 2, 1997

[54] SELF STERILIZING HYPODERMIC SYRINGE AND METHOD

[75] Inventor: Ronald P. Spinello, Red Lion, Pa.

[73] Assignee: Spintech, Inc., Livingston, N.J.

[21] Appl. No.: 619,038

[22] Filed: Mar. 20, 1996

Related U.S. Application Data

[62] Division of Ser. No. 159,664, Nov. 30, 1993, Pat. No. 5,512,730.

[51] Int. Cl.⁶ .................................................. A61M 5/32
[52] U.S. Cl. ........................ 604/199; 604/111; 422/307; 264/525
[58] Field of Search .................. 422/307; 264/525; 604/199, 111; 128/919

[56] References Cited

U.S. PATENT DOCUMENTS

| | | | |
|---|---|---|---|
| 2,629,148 | 2/1953 | Kollsman | 422/307 |
| 3,366,113 | 1/1968 | Hobbs | 604/111 |
| 3,476,506 | 11/1969 | Andersen et al. . | |
| 3,656,480 | 4/1972 | Rubricius | 604/218 |
| 3,892,706 | 7/1975 | Jetzer . | |
| 4,275,628 | 6/1981 | Greenhouse . | |
| 4,315,448 | 2/1982 | Ball . | |
| 4,404,881 | 9/1983 | Hanifl . | |
| 4,409,029 | 10/1983 | Larker et al. . | |
| 4,434,074 | 2/1984 | Fox et al. . | |
| 4,452,251 | 6/1984 | Heilman | 128/655 |
| 4,531,437 | 7/1985 | Szablak et al. . | |
| 4,552,720 | 11/1985 | Baker, Sr. et al. . | |
| 4,628,169 | 12/1986 | Ch'ing-Lung . | |
| 4,662,516 | 5/1987 | Baker, Sr. et al. . | |
| 4,756,681 | 7/1988 | Unger et al. . | |
| 4,820,755 | 4/1989 | Webster | 604/199 X |
| 4,834,917 | 5/1989 | Ramm et al. . | |
| 4,860,958 | 8/1989 | Yermon | 241/23 |
| 4,877,934 | 10/1989 | Spinello . | |
| 4,992,217 | 2/1991 | Spinello . | |
| 5,078,924 | 1/1992 | Spinello . | |
| 5,185,126 | 2/1993 | Adamski et al. . | |
| 5,207,994 | 5/1993 | Suzuki et al. . | |
| 5,256,861 | 10/1993 | Anthony . | |

FOREIGN PATENT DOCUMENTS 2-126632   10/1990   Japan .

Primary Examiner—Michael Powell Buiz
Assistant Examiner—Nguyen At
Attorney, Agent, or Firm—Gottlieb, Rackman & Reisman, P.C.

[57] ABSTRACT

A disposable thermoplastic hypodermic syringe having a hollow metallic needle and thermoplastic body portions at least part of which are formed of temperature calibrated thermoplastic having a full flow liquefaction temperature corresponding to point on the time-death curve for microbial life at which the most resistant spore forms are killed within the time the thermoplastic can be liquefied and resolidified. Heat resistant indicia can be applied to the syringe in a manner to reappear on the solidified thermoplastic mass.

4 Claims, 2 Drawing Sheets

FIG. 1
FIG. 2
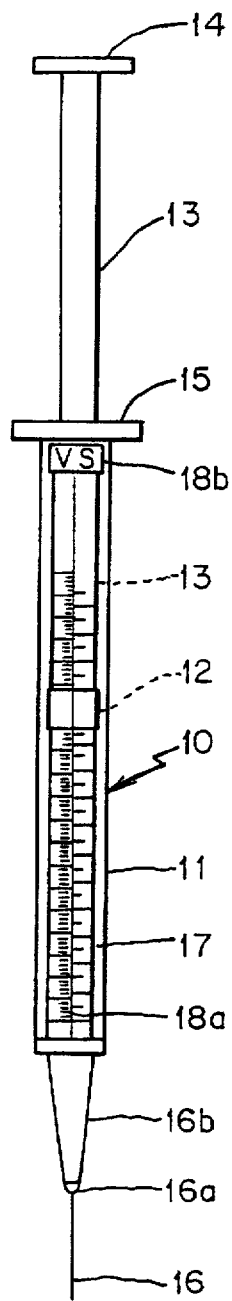
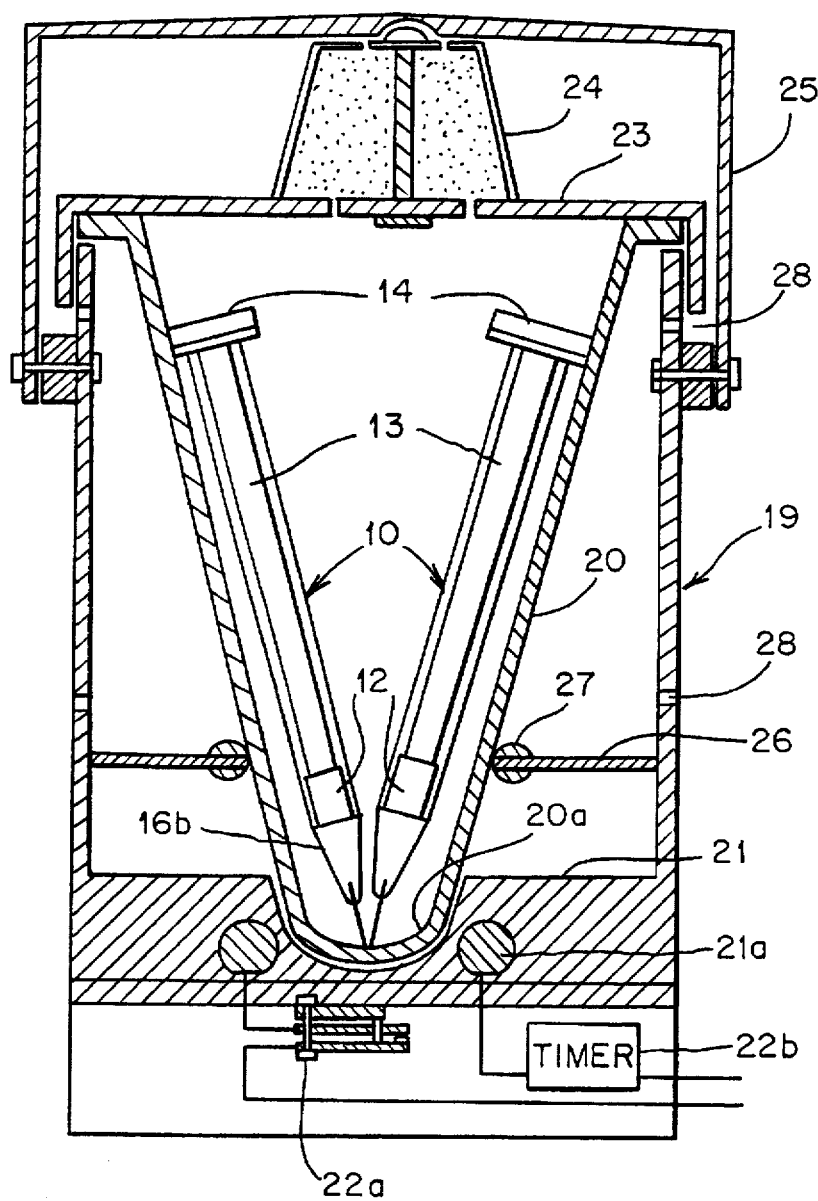

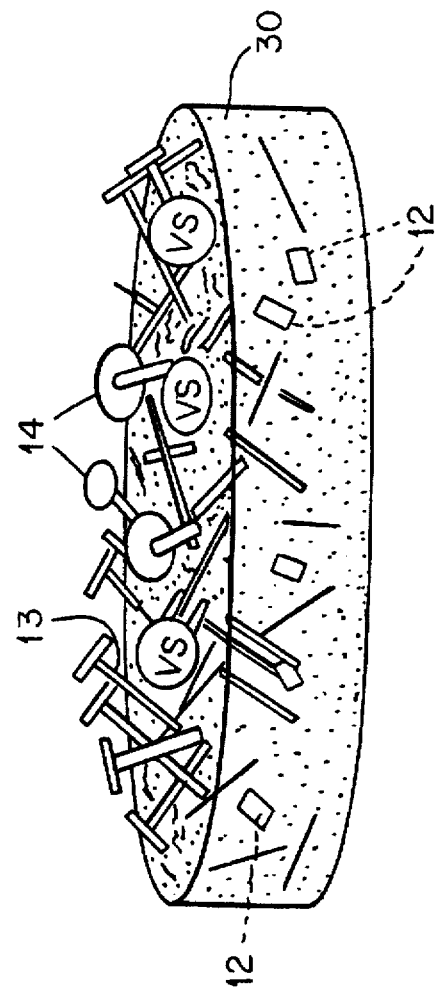
FIG. 4A
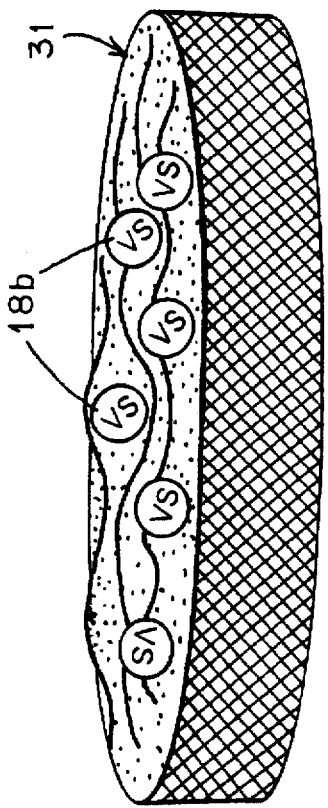
FIG. 4B
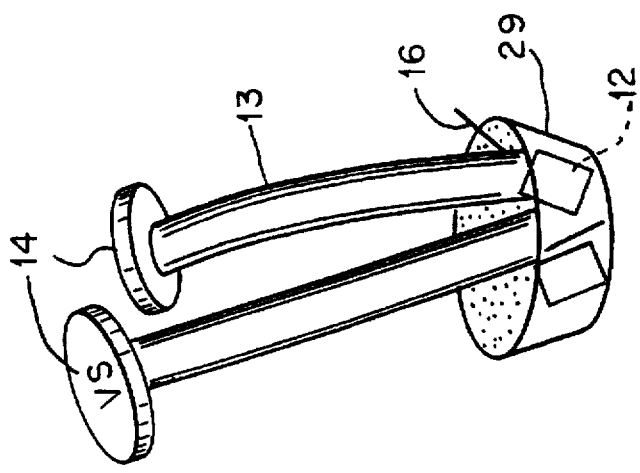
FIG. 3A
FIG. 3B

SELF STERILIZING HYPODERMIC SYRINGE AND METHOD

This is a divisional of application Ser. No. 08/159,664 filed on Nov. 30, 1993 now U.S. Pat. No. 5,512,730.

This invention relates to hypodermic syringes and more particularly to disposable hypodermic syringes which after use are capable of destruction and verifiable self-sterilization at the point of use and, thereafter, disposal as harmless waste.

BACKGROUND OF THE INVENTION

Disposable hypodermic syringes, one of the most widely used medical devices in existence, are also one of the most dangerous to deal with as medical waste. For obvious reasons their use and disposal are subject to regulation at all levels of government. After professional use they are deemed Regulated Medical Waste and the cost for their disposal by licensed handlers under burdens of manifests and regulations which touch every step of the way from the patients they penetrate to the end at either licensed incinerators or special refuse centers. Despite the burdensome efforts of control and the consequent expense to society, there are recurring leaks in the system hazardous to the health of many.

Technology for rendering disposable syringes discernably harmless in a practical, cost-effective way at their point of use has been sought since the time of their acceptance by the medical industry. The first attempts involved simply melting down the thermoplastic parts of the syringes as shown in U.S. Pat. No. 3,958,936, May 25, 1976. Randomly exposed needles, lack of sterility, and lack of means to verify sterility, even if achieved, rendered the waste dangerous and the procedure was abandoned. The art of melting down needles was advanced by Swedish Patent No. 8003576-9, published April 1981, which addressed the problem of randomly exposed needles in the plastic waste by providing supplemental plastic which melted at or below the syringe melting temperature. Sterility and its verifiability remained, however, as a bar to acceptance and use.

Color-changing flags in the form of inks, paints and films which change color when exposed to desired temperatures are used in connection with sterilization and other thermal procedures. They are widely used as an aid to medical professionals to monitor their autoclaves and dry heat sterilizers. If the color has not changed when the heating cycle ends, an otherwise presentable looking scalpel, for example, is not used and recalibration of the sterilizer must be ordered. It is a useful tool for such purposes but it cannot speak beyond its own surfaces. It cannot verify that the heat it felt reached the needle, nor can it deal with time functions. A waste manager bent on mischief for example can easily spot-radiate the patch and proclaim his processed batch sterile at substantial savings of time and energy. It does little good, therefore, for reputable manufacturers to place the most reliable color-changing patch available on medical instruments such as syringes in an attempt to prove the heated or melted down syringes are sterile.

A recent advance in the technology is disclosed in the Applicant's U.S. Pat. Nos. 4,995,217 and 5,078,924 in which verifiable on-site sterilization as waste of various medical items including disposable syringes is achieved by the use of special temperature-calibrated thermoplastic formulated, shaped and arranged to achieve liquefaction or phase change only at a temperature and within a time frame which equals or exceeds the scientifically established and accepted temperature-time death curve for the destruction of all known microbial life, including spore forms, which infect human and other animal life. Sufficient plastic is provided in configurations which insure that molten plastic reaches and covers the needles. The intended purpose of this product cannot be frustrated by either intentional or unintentional error on the part of the processor. Furthermore, if a manufacturer were to be unreliable in the first place, condemning evidence would survive the treatment process.

The present invention represents a further advance in the technology of on-site processing and sterilization of disposable thermoplastic syringes per se by achieving further overall cost reduction, improved verification and simplification of the processing procedure, using the basic technology of U.S. Pat. Nos. 4,995,217 and 5,078,924.

BRIEF SUMMARY OF THE INVENTION

The present invention is based on the teaching of U.S. Pat. Nos. 4,992,217 and 5,078,924 that conventional disposable thermoplastic syringes cannot be reliably or verifiably sterilized by melt-down because they are formed of thermoplastic parts which can be melted and then hardened into a waste mass within a time frame and at temperatures which together fall below the time-temperature death curve for microbial contamination. Verifiable sterilization is, however, shown to be achievable by the use of supplemental temperature-calibrated thermoplastic in the melt-down mass which brings it to a point above the death curve.

The present invention provides a new species of the invention which renders the syringe, in a melt-down process, capable of verifiable self-sterilization by incorporating temperature-calibrated thermoplastic into the syringe itself. One preferred syringe part for incorporation is the plunger stem and thumb-actuator assembly, which undergoes a conspicuous change in geometry upon melt-down while compelling both time and temperature functions which insure sterility. An unmelted plunger stem projecting from a hardened waste mass is conspicuous evidence of incomplete processing and, therefore the possibility of contamination. Other syringe parts can be used. Also in accordance with the invention, verifiability of sterilization of the waste mass after melt-down can be augmented by the addition of or the intensification of pigmentation of the syringe part or parts selected for temperature-calibration. The optical characteristics of the solid waste mass, are discernably modified when melt-down is complete; encapsulated needles can become less visible; and the waste mass can more easily be made self-labelling, i.e. the manufacturer's name, trademark or logo can be made to appear conspicuously in the hardened waste mass. To this end a label of heat resistant material is applied to the syringe as a conventional statement of origin. It must be designed to endure the heat of subsequent processing and also to contrast with the pigmentation of the waste mass. For example, white, heat-resistant lettering in conjunction with a grey or black piston stem will be visible on the unused syringe, whether the label was applied directly to an outer surface of the transparent body portion or directly to the darker stem.

When a single syringe is melted down and hardened the waste mass in lump form will take on a generally dark optical characteristic even though the different plastics, opaque and transparent, of which the syringe is formed do not blend as would a dye for example, in water. The light-colored temperature-resistant label survives meltdown and will not disappear into the dark but will remain visible and contrasting with the dark even if encapsulated within transparent plastic. If many syringes are melted down at once, many more or less discrete dark globules will be dispersed throughout the mass to influence strongly the optical characteristics of the whole as a generally dark mass; many labels will show and few encapsulated needles can be perceived.

The process for melting down the syringes can be tailored to the number of syringes in the load. For processing say 1 to 4 used syringes a small crucible in the shape of an inverted blunted cone is effective to concentrate the molten plastic in a small conical lump of sufficient height to bury the needles. Larger volumes can be processed in generally cylindrical crucibles. Liquefaction from the bottom up is accomplished by using a temperature regulated heating plate at the bottom, contoured to receive the base of the crucible and providing a shielding baffle above the plate to restrict the height of the heated area of the crucible. Cooling can be provided above the baffle to maintain the upper crucible walls at temperatures below liquefaction, allowing the syringes to sink into the mass without a film or flashing of plastic solidifying on the wall. A fitted cover releasably clamped and carrying a filter for any gases which might be generated complete the processing assembly.

BRIEF DESCRIPTION OF THE DRAWINGS

FIG. 1 is a view in side elevation of a disposable hypodermic syringe embodying one form of the invention;

FIG. 2 is a view in vertical section of apparatus for processing the syringes;

FIG. 3A is a view in perspective of a lump of improperly processed waste from two syringes conspicuously revealing by its geometry and other physical characteristics that processing was imperfect and sterility cannot be verified;

FIG. 3B is a view in perspective corresponding to FIG. 3A in which processing to the point of verification of sterility has been achieved.

FIG. 4A is a view in perspective of a waste mass which is the result of imperfect processing in a large cylindrical crucible of a plurality of syringes; and FIG. 4B is a view in perspective corresponding to FIG. 4A in which the overall appearance and geometry verifies sterility and the harmless character of the waste.

Referring to FIG. 1 the invention in a preferred form is embodied in a disposable hypodermic syringe 10, one of many types sold worldwide, in which most of the structure is formed of thermoplastic such as polyethylene or polypropylene formulated to become moldable under heat for processing by various die and molding techniques. The syringe 10 is for purposes of illustration, a design widely used by diabetics for the self-administration of insulin and as such constitutes a significant source of contaminated but functional syringes which find their way, properly or improperly into the regular channels of refuse collection, recycling and dumping which are not in any event suited for handling medical waste.

The syringe 10 comprises a hollow cylindrical body or barrel portion 11 to contain liquid medicaments and formed of transparent thermoplastic through which the liquid can be observed. A lubricated, resilient plunger or piston 12 often formed of a rubber compound slides in the barrel under the control of an attached plunger stem 13 having a thumb-actuator 14 operated in conjunction with an overhanging finger grip 15 to cause liquid to pass through the hollow metal needle 16. The needle is held in a bead or ferrule 16a secured to a hub or adaptor 16b attached to the barrel 11 so that the inner projecting end of the needle is in communication with the liquid chamber 17.

The thermoplastic hollow barrel 11 has relatively thin transparent walls and carries indicia 18a operative in conjunction with the plunger 12 to enable metering of the medication. Identification labelling 18b such as a trademark, grade mark or logo reflecting the origin of the product is formed, in accordance with the invention, of heat resistant material capable of sustaining its integrity and legibility under the heat which melts the substrate on which it is carried. Labels 18b can be affixed for example to the barrel 11, the actuator 14, the stem 13, or the hub 16b of the syringe. The coloring of the labelling is important in relation to the coloring and other optical characteristics of the syringe before and after melt-down, all as described below.

The thermoplastics of which disposable syringes are formed have full flow melting temperatures in the range of 130° to 150° C. In accordance with the invention at least a portion of the syringe, for example, one or more parts among the stem 13, actuator 14 and hub 16b, are formed of a temperature-calibrated plastic having full flow melting temperatures above and differing substantially from those of the remaining, if any, syringe parts. The entire syringe including the body portion or barrel 11 can be formed of such material but for a number of reasons, including transparency, is a less desirable part. The temperature of liquefaction selected for processing is a parameter which must be respected to prevent vaporization, burning and other environmentally adverse effects during processing as waste. Temperatures in the range of 180° to 200° C. have been found acceptable for practicing the invention using presently available materials.

Other desirable features of the temperature-calibrated plastic are safe toxological and ecological characteristics and increased crystalinity, the latter yielding snap phase changes between solid and liquid. A saturated linear copolyester such as that sold under the trademark DYNAPOL is an example of the thermoplastic useful in the practice of the present invention. Others are available or can be formulated. Examples of the use of the effects of the temperature calibrated plastic in various parts of the syringe are described below. It should be noted that syringes are relatively small devices with relatively small masses of material being required for fabrication. Syringe parts will, therefore, melt relatively quickly so that the designer of a self-sterilizing syringe in accordance with the invention has a much lower minimum possible time factor to work with than does the designer of a sterilizing system in which more massive charges of temperature-calibrated plastic can be used.

The stem 13, which is out of contact with the liquids in the syringe preferably includes relatively dark pigmentation achieved for example by carbon black which can be tempered with white to form a grey which contrasts to the rest of the syringes and is capable of modifying the appearance of the final waste product when the syringe is melted down to produce a self-sterilized, self-verifying mass encapsulating the needle.

The pigmentation is also selected to contrast with a label 18b which is applied to the actuator 14 or the outside wall of the syringe barrel 11 or both. In accordance with the invention the label 18b can be colored white to contrast with the darker pigmented stem. It can also be applied directly to the stem, or to other parts such as the hub 16b but in all cases it should be made of a material which maintains its integrity and appearance through the highest possible temperature to which the syringe will be subjected in the thermal process.

Thermosetting inks and paints, for example, can be used. The mechanics of the label reappearing in the final waste mass after melt-down are described below in conjunction with the melt-down process.

Referring to FIG. 2, two used contaminated syringes 10 are shown in a relatively small thermal processor 19 having a contoured, melt-down crucible 20 formed for example of teflon-lined drawn aluminum for receiving the syringes. An inverted conical configuration with a blunted apex 20a will concentrate the final mass into a lump of sufficient height to exceed the needle length to ensure encapsulation. The lower end 20a of the crucible 20 is received in a contoured heating plate 21 of substantial mass for heat regulation and concavely contoured to match the crucible geometry. An electrical resistance heater 21a under the control of a thermostat 22a and timer 22b provide the heat source for the plate 21. A cover portion 23 containing a filter 24 is latched in place in a gas tight seal over the crucible by a pivotally mounted handle or bail 25 which releasably latches over the filter. An internal baffle plate 26 with a resilient seal 27 engages the crucible near its lower end to confine convection currents to the lower end. Cooling vents 28 are provided for the space above the baffle plate. If desired a bi-metal flapper valve (not shown) can be provided in the baffle to close automatically during the heat cycle and to open during the cooling cycle. Thus the waste load melts from the bottom up while the upper area is kept cool, preventing molten plastic from being wiped onto the upper walls of the crucible and creating troublesome flashing.

The time frame within which the temperature-calibrated plastic changes phase in the shortest theoretically possible interval and the temperature reached are the two variables which position the process on the time-death curve for microbial life. See "Disinfection, Sterilization and Preservation: by Seymour S. Block, Lea and Fibger 1993, which establishes that within stainless steel surfaces (an experimental model for the space within a hollow hypodermic needle) a temperature of approximately 190° C. achieves instantaneous death. As temperature declines, the time in which total death occurs rises so rapidly it is often shown on a logarithmic scale. Below 150° C. the time reaches so many hours that it is no longer an option for sterilization processes.

In accordance with the invention, therefore, a determination must be made of the least possible time within which melt-down and resolidification of the waste mass (two successive phase changes) can possibly occur, given the most time-and-thermal efficient heat exchange methods and apparatus known, and working within vapor temperature limits that preclude serious vaporization, gassing off, or even ignition of the waste.

The form factor of the part or parts made of temperature-calibrated plastic plays a part in the equation, with a thin, sheet-like member with large exposed surface areas having a shorter time constant for phase change than, say, a solid cylindrical member such as the stem 13.

Whereas it is a relatively simple matter to melt down a conventional disposable thermoplastic syringe and to solidify it into a lump without sterilizing i.e., reaching the time-death curve, a design using the principles of the invention can provide a syringe that cannot be melted down and solidified into a lump without achieving sterilization. It is possible to design a syringe in which sterilization is necessarily achieved at the instant of melt-down, with any time that follows being a safety factor.

Moreover, the invention provides for visual verification of an unsterilized waste mass. If the syringe 10 is processed at a temperature setting of say 155° C. for enough time (plus any amount more time) to melt down the syringe barrel into a lump as shown in 3A, the temperature-calibrated plastic stem 13 and actuator 14 will survive as an indicator of non-sterility. On the other hand, if the process is carried out in the fastest way possible to achieve melt-down of the stem and actuator and then solidification as shown in FIG. 3B, the time-death curve will have been exceeded and sterility assured. It should also be noted that it is possible to achieve sterilization of the mass without melting the stem and actuator. If for example, the waste is heated to 160° for, say, half an hour, achieving melt-down of all but the stem and actuator, the appearance of FIG. 3A will result even though the mass is sterile. But a half-hour is a finite time, and 160° a finite temperature both of which are unverifiable by the appearance of the final product. Time and temperature of themselves are unverifiable functions after the fact; the best clocks and the best thermometers can break down even in the hands of the most reliable operator, and the end product will not readily reflect the error. The temperature calibrated plastic is not subject to these problems; if it has not melted, infection can be present, if it has melted microbial infectious matter cannot be present within the mass. If the temperature-calibrated plastic has been erroneously calibrated, whether deliberately or intentionally, it remains in the waste to reveal the error.

It is possible as well as desirable, therefore, to provide labelling which follows the syringe from its inception through the thermal processing. The label 18b being impervious to the heat will survive in the mass 29 of FIG. 3A. The white indicia will be somewhat visible in the more or less transparent jump 29, effected optically only by the plungers 12 at the ends of the stems 13. The needles 16 are also visible. In FIG. 3B, however, the entire lengths of the pigmented stems 13 have become two large randomly shaped dark masses within the lump, although not fully blended, they constitute a relatively large percentage of the whole even though partly immersed in the transparent plastic of the body portion. Optically, the mass appears essentially dark. The white indicia 18b in the generally dark mass will not except in rare cases be obscured but will stand out in contrast to it. The indicia on the actuator 14 will almost always appear on the top surface of the processed lump. Thus, the origins of the temperature-calibrated plastic and the syringes themselves can be traced. The needles will be relatively obscured.

Referring to FIGS. 4A and 4B there are illustrated solidified waste masses 30 and 31 which are the result of processing in generally cylindrical crucibles (not shown) of a plurality of syringe 10, say on the order of fifty. The lump or mass 30 is primarily clear or transparent plastic with stems 13 and actuators 14 projecting randomly. Needles 16 and pistons 12 can be perceived as can to some extent the labels 18b. Sterility is possible but in no way certain or verifiable. In FIG. 4B the myriad of more or less discrete dark amorphous shapes so permeate the while that optically it is perceived as more or less uniformly dark. The needles 16 are less visible; the black pistons 12 blend in; and the white labels 18b stand out conspicuously at many points at any angle of view. The mass 31 is verifiably sterile, harmless, and no longer constitutes Regulated Medical Waste.

As disclosed above, it is also possible to fabricate the hubs or adapters 16b of temperature-calibrated plastic. This mode of the invention differs from that in which the stem 13 is formed of temperature-calibrated plastic. Referring to FIG. 2, it will be seen that the used syringes are standing on their needles 16 with the needles being held by their hubs 16b. The heat at the base of the crucible will conduct upward through the needles and the hot air will convect upward. If the temperature is below that called for to achieve verifiable sterilization, the hubs 16b will not melt, either by conduction or convection. It will take a long time for the body or barrel 11 to soften and melt, if at all, giving the operator evidence that the thermostat, for example, may have malfunctioned. If the barrel eventually melts down and if the needles hold firm in hubs (it is possible to render them releasable by using meltable plastic seals or ferrules 16a or to render them fixed by using, for example, metal ferrules) the combined length of the exposed needle and the hub will project above the rest of the melted down syringe, assuming the stem and actuator are formed of conventional syringe plastic. The length of hubs without the needle extension is normally sufficient to exceed the height of the solidified lump. Thus, evidence of possible failure to sterilize is presented to the operator and others in the waste handling chain. This feature is not available in a system in which a large number of syringes is placed in a wide cylindrical crucible where they can become horizontal; it is most useful when one or two syringes are melted down in the small, contoured crucible 20.

While the invention has been disclosed above, referring to preferred embodiments, it will be understood that it can take other forms and arrangements without departing from the scope of the invention. For example, the labels 18b can be made dark and the stem 13 pigmented in white to contrast. Also, more sophisticated temperature controls can be used for the processor to speed processing. Since the needles 16 initially hold the syringes from the crucible walls (see FIG. 2), the initial temperatures can be set higher, well into the range at which burning and gassing of the plastic and rubber pistons would normally occur, and then subsequently lowered. Temperatures can also be maintained higher while the phase change is occurring, with the augmented heat absorption of liquefaction of the plastic preventing the plastic mass from reaching dangerous temperatures. Also, while the invention has been described having reference to thermoplastic hypodermic syringes, it is applicable to other thermoplastic medical hypodermic devices such as disposable scalpels in which the handle can be temperature-calibrated plastic, the melt-down of which can verify the sterilization of the blade and, when provided in sufficient volume, encapsulation of the blade. The invention should not therefore be regarded as limited except as set forth on the following claims.

What is claimed is:

1. A disposable hypodermic syringe comprising a hollow needle and predominantly thermoplastic body and actuating portions to contain and pass liquids through the needle, at least a portion of the syringe being temperature-calibrated to liquify at or above the temperature which destroys all body-inhabitating microorganisms and their spore forms within the time frame that thermal liquefaction and subsequent hardening of the thermoplastic can be achieved, said portion being temperature-calibrated by selection of a thermoplastic material having a suitable melting point and by selection of both a form factor and a phase change time constant for the portion which insure sufficient time at the melting point to achieve destruction of the micro-organisms and their spore forms, said temperature-calibrated plastic including substantial pigmentation contrasting with the other thermoplastic of which the syringe is formed, whereby melting of the syringe necessarily achieves sterilization of the resulting waste mass, and whereby substantially complete thermoliquifaction and subsequent hardening of all thermoplastic results in an optical blending of the pigmentation with the resultant hardened waste mass to afford a visual indication that the waste is sterile.

2. A disposable hypodermic syringe as set forth in claim 1 including label means substantially indestructible at all processing temperatures and formed to contrast visually with said pigmentation, the label means being affixed to at least one of the body portion and the actuating portion.

3. A disposable hypodermic syringe as set forth in claim 1 in which the actuating portion includes an actuator stem, said temperature-calibrated portion including the actuator stem, the liquefaction and subsequent hardening of which results in a visual geometric change of the actuator stem.

4. A disposable hypodermic syringe as set forth in claim 3 in which the body portion is at least partially transparent and the actuator stem is relatively heavily pigmented, whereby substantially complete liquefaction and subsequent hardening of all thermoplastic results in an optical blending of pigmentation into resultant hardened waste mass to afford, together with the liquefaction and change of shape of the stem actuator, a visual indication that the waste is sterile.

* * * * *